(12) United States Patent
Shyu et al.

(10) Patent No.: US 7,355,713 B2
(45) Date of Patent: Apr. 8, 2008

(54) METHOD FOR INSPECTING A GRATING BIOCHIP

(75) Inventors: Deh Ming Shyu, Miaoli County (TW); Chun Hung Ko, Changhua County (TW); Yi Sha Ku, Hsinchu (TW); Nigel Smith, Hsinchu (TW)

(73) Assignees: Industrial Technology Research Institute, Hsinchu County (TW); Accent Optical Technologies, Inc., Bend, OR (US)

( * ) Notice: Subject to any disclaimer, the term of this patent is extended or adjusted under 35 U.S.C. 154(b) by 0 days.

(21) Appl. No.: 11/615,886

(22) Filed: Dec. 22, 2006

(65) Prior Publication Data

US 2007/0156349 A1 Jul. 5, 2007

(30) Foreign Application Priority Data

Dec. 30, 2005 (TW) ............................... 94147872 A

(51) Int. Cl.
*G01N 21/47* (2006.01)

(52) U.S. Cl. ..................... 356/446; 356/326; 356/445; 356/451; 385/4; 385/12; 385/14

(58) Field of Classification Search ................ 356/326, 356/369, 445–446, 451; 385/4, 12, 14–16
See application file for complete search history.

(56) References Cited

U.S. PATENT DOCUMENTS

2003/0113766 A1* 6/2003 Pepper et al. ................... 435/6
2006/0193550 A1* 8/2006 Wawro et al. ................ 385/12

* cited by examiner

Primary Examiner—Layla G. Lauchman
Assistant Examiner—Iyabo S Alli
(74) Attorney, Agent, or Firm—WPAT, P.C.; Anthony King

(57) ABSTRACT

A method for inspecting a grating biochip comprises the steps of irradiating a grating biochip using a light beam, measuring a diffracted light using a photodetector, selecting a plurality of parameters of the grating biochip, and optimizing the parameters to enhance the detection sensitivity, wherein the diffracted light is generated by the light beam passing the grating biochip. The grating biochip comprises a grating structure including a semiconductor substrate, a grating positioned on the semiconductor substrate and a dielectric layer covering the grating and the semiconductor substrate. The sample of the biochip is positioned on the grating structure.

18 Claims, 7 Drawing Sheets

METHOD FOR INSPECTING A GRATING BIOCHIP

BACKGROUND OF THE INVENTION (A) Field of the Invention

The present invention relates to a method for inspecting a grating biochip, and more particularly, to a method for inspecting a grating biochip using an optical inspection instrument.

(B) Description of the Related Art

The development of the biological technology field has directly affected the quality of human life, and has become a significant field of current scientific research. The development of the biochip has attracted significant attention due to its wide applications including medical inspection fields such as gene-analyzing and gene-sequencing research, the inspection for disease medications and the inspection of the properties of Chinese herbal medicine.

The conventional biochip inspection using the fluorescence technique has good detection sensitivity, but requires a complicated fluorescence labeling experiment to be performed in advance, and the fluorescence itself has unexpected risk of contaminating the sample under inspection. These factors affect the reliability of the experiment. A label-free inspection method has been proposed for solving these problems. Recently, label-free inspection methods have been proposed in succession, wherein the surface plasma resonance (SPR) attracts much attention due to its good detection sensitivity, but the inspection cost is relatively high since it requires the surface of the prism to be coated with a metal film. The prism coupled SPR is shown in FIG. 1, the surface between a sample 101 and a prism 103 must be coated with a metal film 102, and requires a TM-mode light source 105. Therefore, the cost is relatively high, only one single sample can be measured at a time, and the requirements of arranging the biochips in an array and inspecting multiple samples at a time cannot be satisfied.

Using an angular scatterometer to inspect a biochip is an innovative technique. The angular scatterometer has a good repeatability and reproducibility, and possesses many advantages such as optical non-destructiveness, quickness of use, and mass measurement. The surface plasma resonance is a method having the higher sensitivity for label-free biochip inspection, and it can be seen from the preliminary simulation result that the angular scatterometer and the surface plasma resonance have the same level of detection sensitivity. Thus, the angular scatterometer in fact has the potential to be developed as a quick and mass biochip inspection method having high sensitivity.

Recently, label-free inspection draws more and more attention in the biological sample inspection fields outside the conventional fluorescence method, since the complicated labeling process can be omitted and the problem of sample contamination no longer exists. Surface plasma resonance has the longer development history and is the method with the higher detection sensitivity of the current label-free measurement methods, which can be classified into a prism coupled SPR and a grating coupled SPR according to different excitation methods for the surface plasma resonance. The detail of the prism coupled SPR can refer to the disclosure of Raether H. (see: Surface plasma oscillations and their applications. In: Hass G, Francombe M, Hoffman R, eds. Physics of thin films. New York, N.Y.: Academic Press, 1977 vol. 9, p 145-261), while the detail of the grating coupled SPR can refer to the disclosure of Jennifer M. Brockman and Salvador M. Fernadez (see: Grating-coupled surface plasma resonance for rapid, label-free, array-based sensing, American Laboratory, June 2001, p 37-40).

SUMMARY OF THE INVENTION

The present invention provides a method for inspecting a grating biochip comprising the steps of irradiating a grating biochip using a light beam, measuring a diffracted light using a photodetector, selecting a plurality of parameters of the grating biochip, and optimizing the parameters to enhance detection sensitivity, wherein the diffracted light is generated by the light beam passing the grating biochip. The grating biochip comprises a grating structure including a semiconductor substrate, a grating positioned on the semiconductor substrate and a dielectric layer covering the grating and the semiconductor substrate. The sample of the biochip is positioned on the grating structure.

The present invention proposes using the angular scatterometer to inspect the biochip having the sample on the grating structure including periodical positioned gratings, and optimizing parameters such as the period, the line space ratio and the thickness of the grating, using rigorous coupled wave algorithm (RCWA). According to the preliminary simulation result, the detection sensitivity of the present invention is slightly higher than that of the prism coupled SPR. In addition, the fabrication cost of the biochip for the present invention is lower than that for the prism coupled SPR since the present invention does not require a metal film to be coated on the sample under inspection. Furthermore, the present invention allows different biological samples to be fabricated on a single substrate, and thus adapted for a mass and quick inspection. In addition, the complicated fluorescence labeling experiment for the conventional fluorescence inspection can be omitted; thus the present invention can save time.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
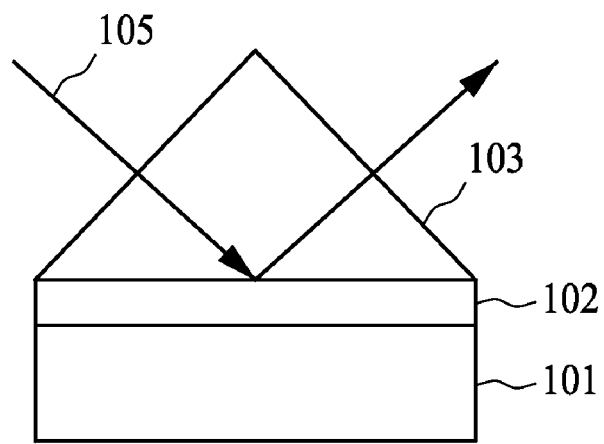
FIG. 1 shows a conventional prism coupled surface plasma resonance inspection.
Figure 2:
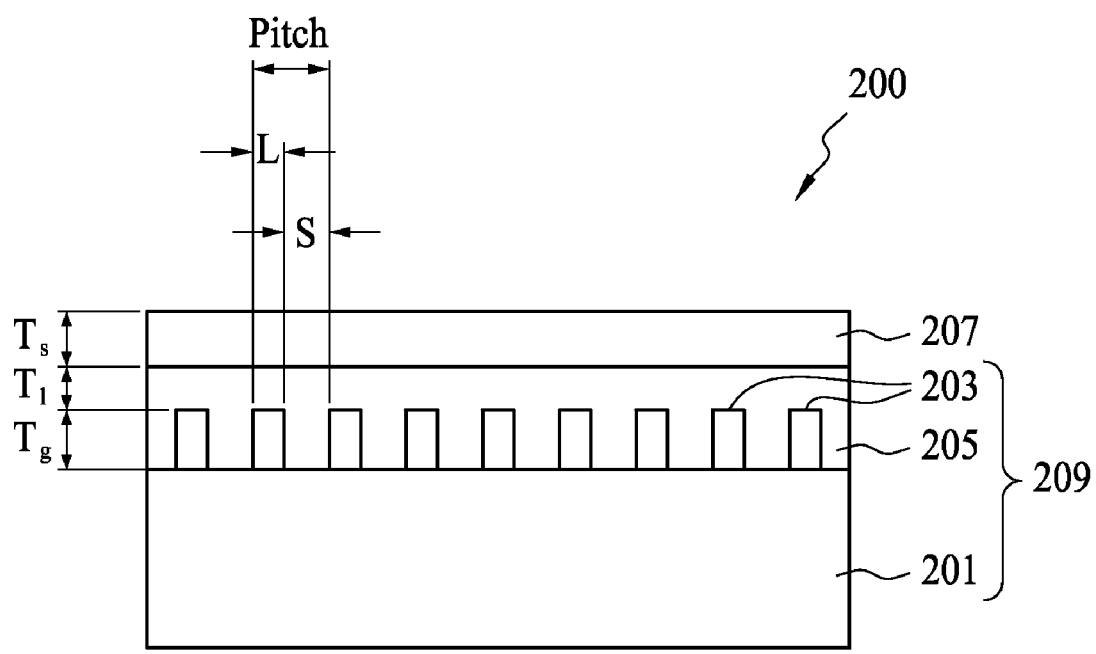
FIG. 2 illustrates a biochip according to one embodiment of the present invention.

The present invention proposes using an angular scatterometer as the optical system architecture and the rigorous coupled wave algorithm (RCWA) as a basis instead of the common grating-calculating method based on zero order. FIG. 2 illustrates a biochip 200 according to one embodiment of the present invention. The biochip 200 includes a grating structure 209 and a sample 207 under inspection positioned on the grating structure 209. The grating structure includes a silicon substrate 201, a grating 203 made of silicon-oxygen compound and a dielectric layer 205 made of silicon-nitrogen compound. The grating 203 made of silicon-oxygen compound is periodically positioned on at least one dimension of the silicon substrate 201, the dielectric layer 205 covers the grating made of silicon-oxygen compound and the silicon substrate 201, and the dielectric layer 205 can be made of a poly-silicon material as well, wherein the dielectric constant of the dielectric layer 205 is higher than that of the grating 203.

The thickness of the grating 203 made of silicon-oxygen compound is Tg, the line width is L, the space between two lines is S, the total thickness of the dielectric layer 205 is T1+Tg, and the thickness of the sample 207 is Ts. The biochip 200 can be fabricated using the semiconductor fabrication process, for example, the grating structure 209 with the regularly arranged grating 203 of silicon-oxygen compound can fabricated on the silicon substrate 201 using lithographic and etching processes. In addition, since many biochips 200 with the grating structures 209 can be fabricated on a wafer, which can be configured to perform mass biochip sample inspections, and the biochips 200 on the wafer can be arranged in a one-dimensional or two-dimensional array.

FIG. 3 (a) illustrates a biochip sample inspection system 300 according to one embodiment of the present invention. The biochip sample inspection system 300 includes a light source 301, a biochip 200 and a photodetector 303. The light source 301 is configured to produce a light beam having a predetermined wavelength such as 632.8 nm, the biochip 200 carrying the sample 207 under inspection can scatter the light beam, and the photodetector 301 is configured to receive the light beam scattered by the sample 207 of the biochip 200 under inspection. The light source 301 can be a laser source such as a linear laser source or a planar laser source. Preferably, the light source 301 is a focused laser source with the laser wavelength between 100 nm and 1000 nm. In particular, the measurement signal generated by the photodetector 303 is a function of an incident angle of the light beam and structural parameters of the grating 203 of the biochip 200.

Figure 3A:
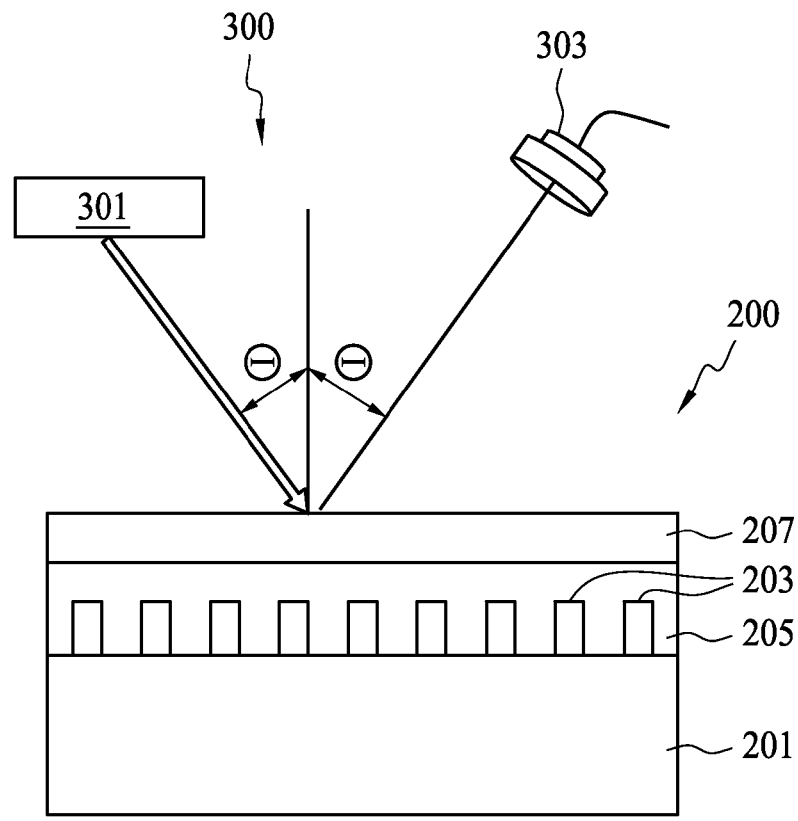
FIG. 3(a) illustrates a biochip inspection system according to one embodiment of the present invention.
Figure 3B:
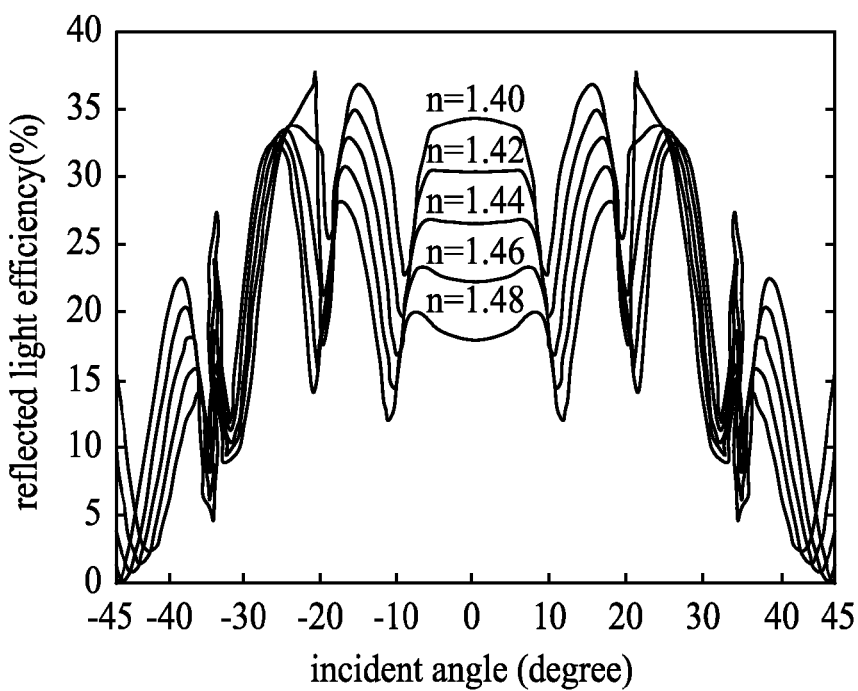
FIG. 3(b) illustrates a signature obtained by inspecting a biochip sample using the inspection system shown in FIG. 3(a)

As shown in FIG. 3(a), as the light beam irradiates the sample 207 under inspection on the grating structure 209 having periodically positioned gratings 203 at a plurality of incident angles, the zero-order diffraction light is received by the photodetector 303. The receiving angle of the photodetector 303 changes as the incident angle changes, and the angular scatterometer is also referred to as a (2-θ) optical system architecture. The acquired signature is shown in FIG. 3(b), wherein the x-axis represents the incident angle, and the y-axis represents the diffraction light efficiency. Since the refractive index of the sample 207 after the reaction is different from that before the reaction, the signature is changed and thus different, and the variation of the refractive index before and after the reaction of the biological sample 207 can be obtained by calculating the variation of the peak angle position of the diffraction light intensity of the signature.

Figure 4:
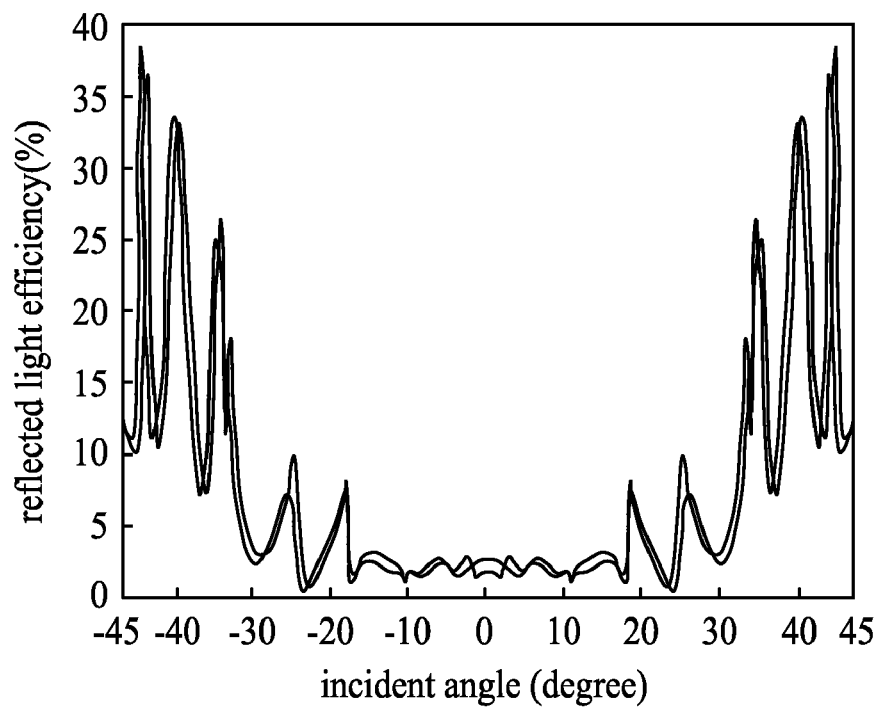
FIG. 4 illustrates a diffraction light spectrum of the angular scatterometer as the variation of the sample refractive index is 0.01.
Figure 5:
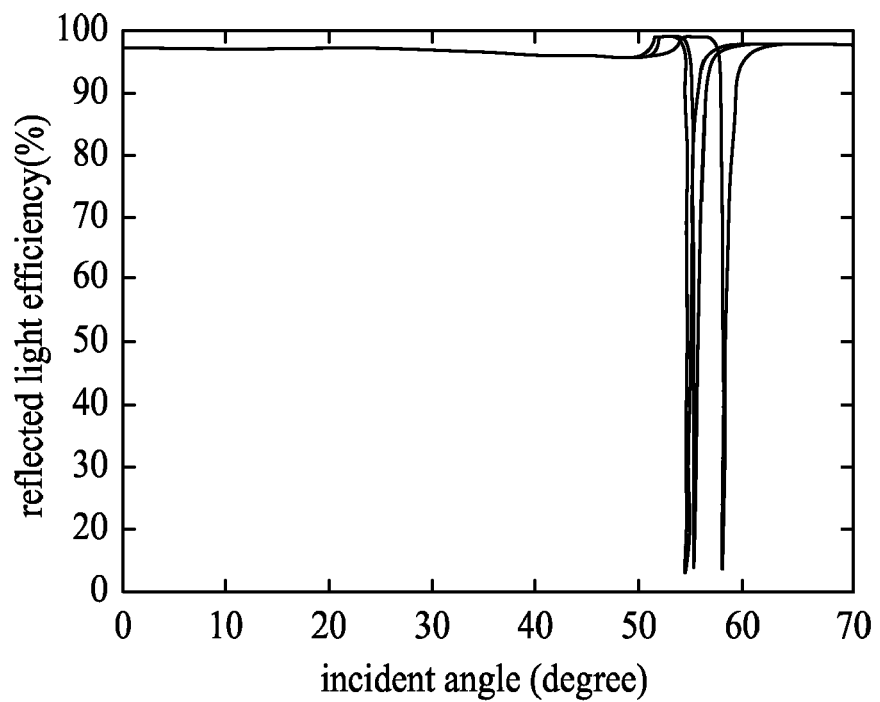
FIG. 5 illustrates a diffraction light spectrum of the prism coupled surface plasma resonance as the variation of the sample refractive index is 0.01.

The wavelength of the incident light of the angular scatterometer is 632.8 nm, and the simulated incident angle is between −45° and +45°. In this embodiment, the nominal refractive index of the biological sample 207 is 1.40, the thickness is 1000 nm (corresponding to Ts in FIG. 2). The period, line space ratio (L/S) and thickness (T) of the grating 203 made of silicon dioxide ($SiO_2$) on the silicon substrate 201 is designed by optimization simulation such that the optimal detection sensitivity is achieved and the optimization method is not limited by the different material of the sample 207. In addition, the grating 203 is covered by the silicon nitride ($Si_3N_4$) layer 205 having a higher refractive index with a thickness of 400 nm (corresponding to T1+Tg in FIG. 2) to avoid reducing the intensity of the diffraction light due to the occurrence of the antireflective effect. FIGS. 4 and 5 show the diffraction light signatures of the angular scatterometer and the prism coupled SPR, respectively. The variation of the refractive index of the biological sample 207 is 0.01, the x-axis represents the incident angle, and the y-axis represents the diffraction light efficiency.

Figure 6:
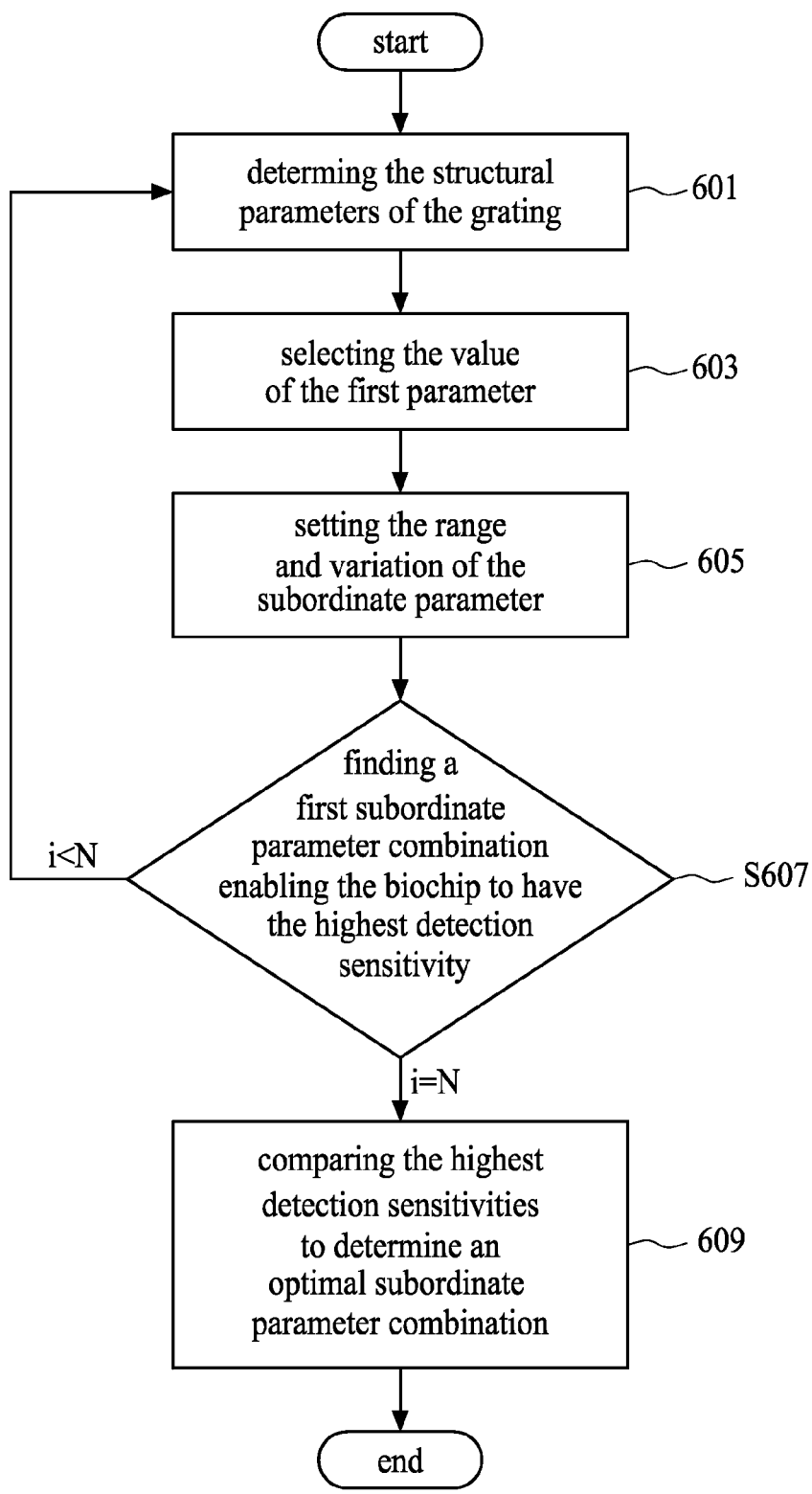
FIG. 6 illustrates a flow chart showing an optimization method for the biochip according to one embodiment of the present invention.

FIG. 6 illustrates the optimization method of the grating structure 209 of the biochip 200 based on the rigorous coupled wave algorithm (RCWA). First of all, in Step 601, parameters (such as the period, the line space ratio, thickness of the grating, and the thickness of the dielectric layer) of the grating structure 209 can be added into the simulation as determined. In Step 603, the value of the first parameter (the period of the grating 203 as shown in FIG. 6) is determined to be Pi (i represents an integer such as 1, 2, . . . n−1, n, n+1, . . . N−1, N); in other words, this value is an initial value or the value after one simulation. After the value of Pi is determined (assuming Pn), in Step 605, the ranges and variations of the second and third parameters (subordinate parameters) are set. In FIG. 6, the second and third parameters are the line space ratio (L/S) and the thickness (T), respectively. The line space ratio L/S is 0, R1, R2 . . . Rm . . . 1 with the variation being the absolute value dR of Rm−Rm−1, and the thickness T is 0, R1, R2 . . . Rm with the variation being the absolute value dT of Tm−Tm−1.

Figure 7:
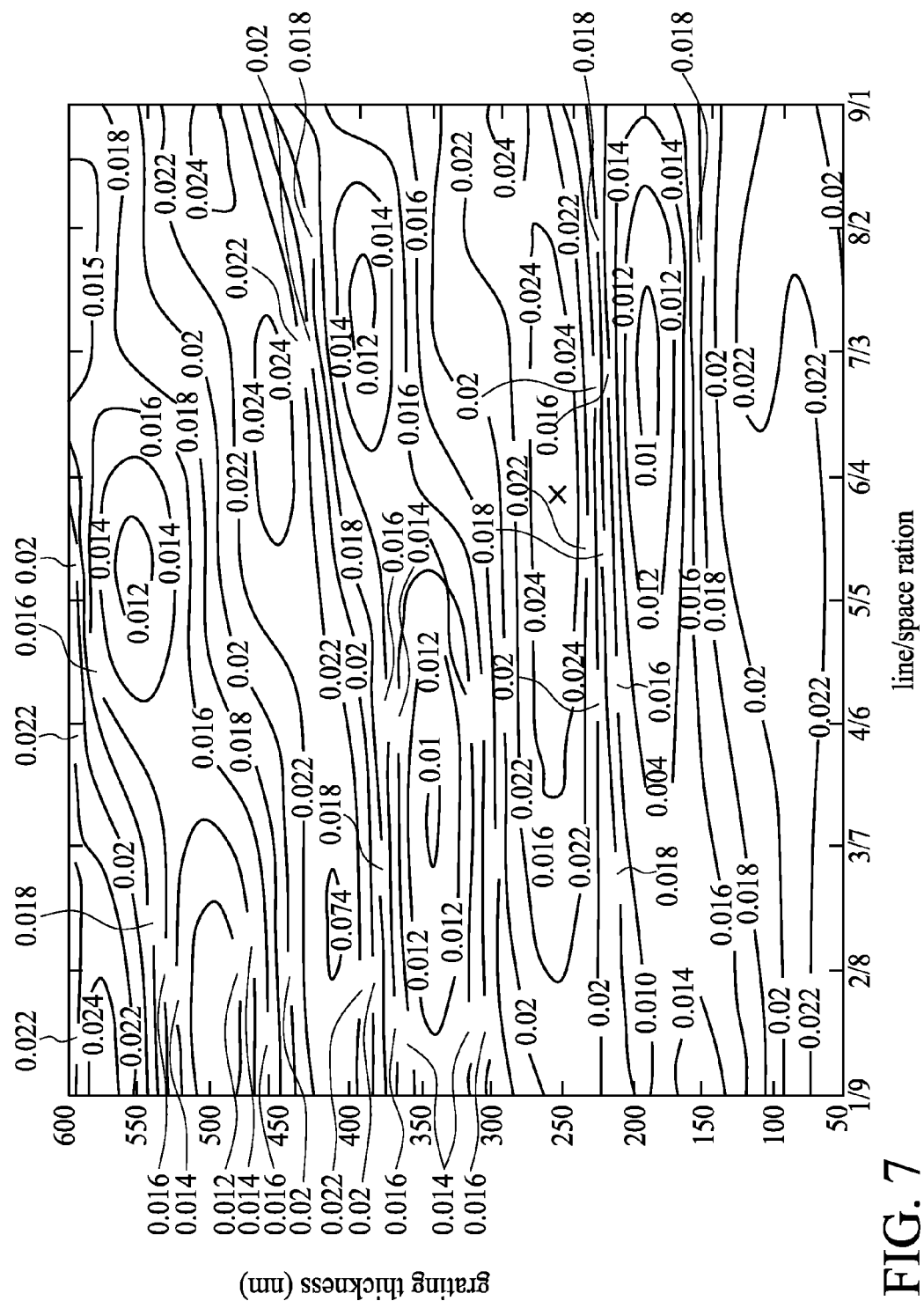
FIG. 7 illustrates a sensitivity distribution diagram of each subordinate parameter combination obtained by RCWA at fixed primary parameters.
Figure 8:
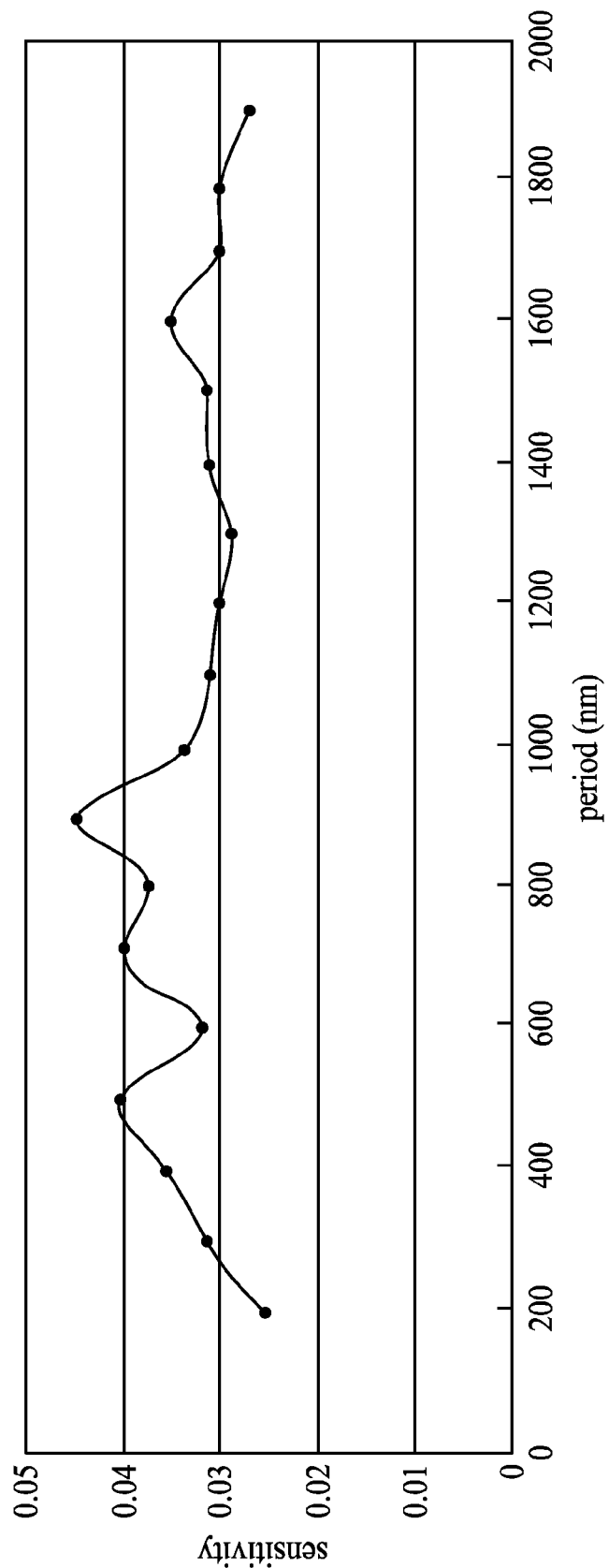
FIG. 8 illustrates a distribution diagram of the sensitivity corresponding to the primary parameter obtained by integrating multiple sensitivity distribution diagrams.

Subsequently, each possible combination of the second parameter and the third parameter is simulated by RCWA to calculate the inspection sensitivity of the biochip 200. The simulation result is shown in FIG. 7, which is a simulation diagram obtained when Pi is 200 nm, wherein the x-axis represents L/S with the range between 0 and 1, and the y-axis represents the thickness of the grating Tg with the range between 0 nm and 600 nm. The numeral inside FIG. 7 stands for the inspection sensitivity of the biochip 200, and each point on each curve has the same inspection sensitivity. After that, in Step 607, the combination of the second parameter, the third parameter, etc. of a highest inspection sensitivity when the first parameter is a certain value is determined. In FIG. 6, an optimal sensitivity and the optimal combination (L/S, T)I of the line space ratio L/S and the thickness T under a Pi value (assuming Pn) is determined, and the variation dP of Pi is adjusted, and then the simulation of the next period (Pn+1) is performed. The above-mentioned steps are repeated N times; N simulation diagrams as shown in FIG. 7 can be obtained (each Pi has a simulation diagram). Each parameter combination of the optimal sensitivity can be picked out from each simulation diagram, and FIG. 8 is obtained by combining N optimal sensitivities under the Pi value. An optimal combination of (P, L/S, T) can be obtained by analyzing FIG. 8; it should be noted that if necessary, a detailed simulation (with a smaller variation dP) can be further made near Pn of the optimal sensitivity in N Pi values, so as to obtain a highest sensitivity.

Figure 9:
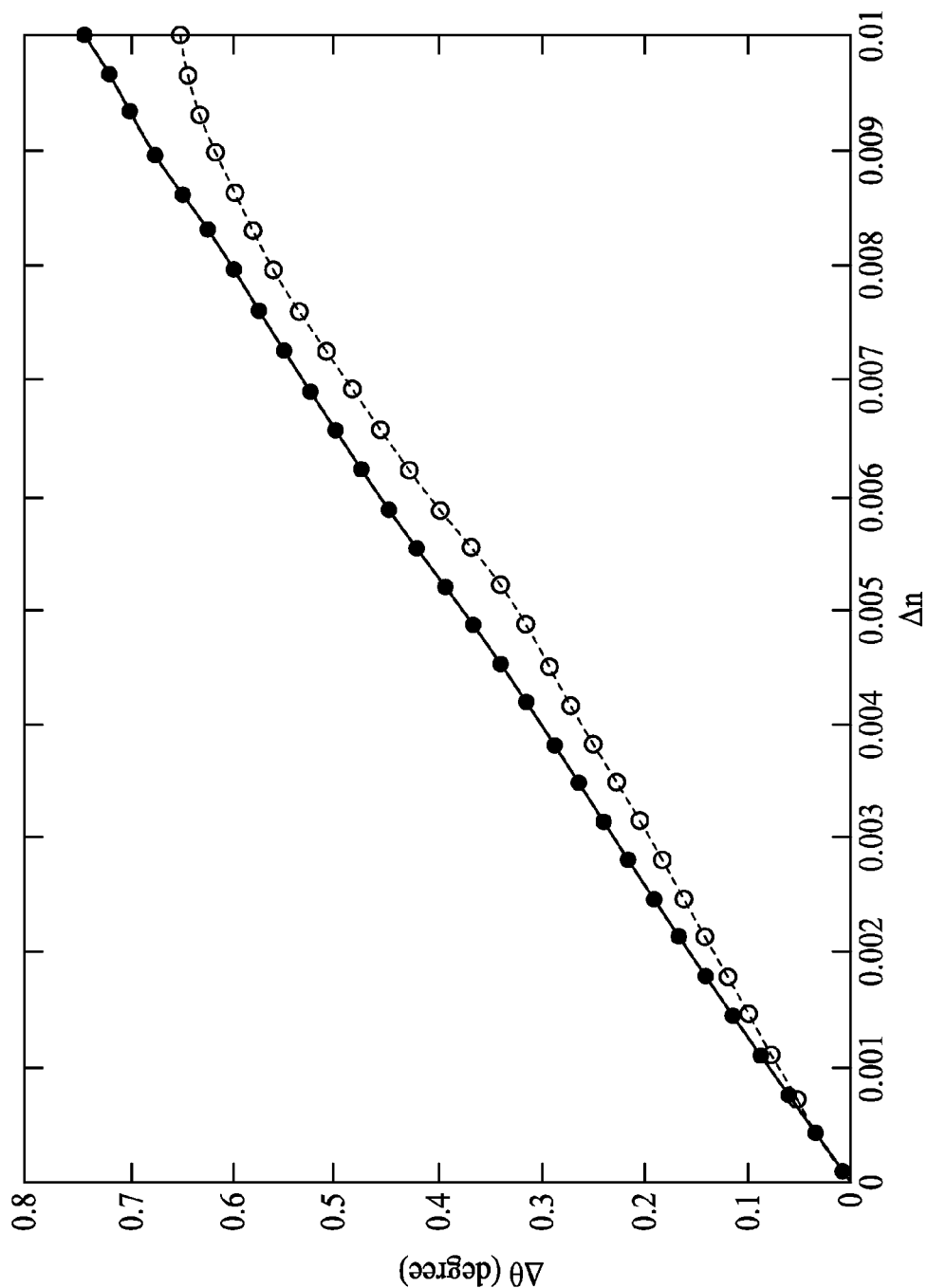
FIG. 9 illustrates a comparison result for measurements of the biochip sample by the angular scatterometer and the prism coupled surface resonance.

FIG. 9 is a simulated comparison result of measurements for the sample 207 of the biochip 200 using the angular scatterometer and the prism coupled SPR system, respectively. The x-axis represents the variation Δn of the refractive index of the biological sample 207, the y-axis represents the variation Δθ of the peak angle of the diffraction light, and the nominal refractive index of the biological sample 207 is 1.4. The result shows that the measurement sensitivities of the two methods are close. However, if the mass production and mass measurement are taken into account, the present invention is better than the prism coupled SPR since the present invention requires fabrication of only the grating structure 209 for carrying the sample 207 for the angular scatterometer, and the grating structure 209 can be fabricated in a mass production by the semiconductor fabrication process, which has a lower cost. In contrast, the prism coupled SPR requires coating of a metal film on each sample under test and thus has a higher cost. Furthermore, since the angular scatterometer uses a focused laser source, the standard size of the measured sample is only 85×60 μm$^2$, which can meet the requirements of arranging the biochip 200 in an array manner and measuring multiple samples 207 at a time and thus achieves mass measurement.

The present invention proposes using the angular scatterometer to inspect the biochip having the sample 207 on the grating structure 209 including periodical positioned gratings 203, and optimizing the parameters such as the period, the line space ratio and the thickness of the grating 203, using rigorous coupled wave algorithm (RCWA). According to the preliminary simulation result, the detection sensitivity of the present invention is slightly higher than that of the prism coupled SPR. In addition, the fabricating cost of the biochip 200 for the present invention is lower than that for the prism coupled SPR since the present invention does not require coating of a metal film on the sample under inspection. Furthermore, the present invention allows different biological samples 207 to be fabricated on a single substrate 201, and thus is adapted for a mass and quick inspection. In addition, the complicated fluorescence labeling experiment for the conventional fluorescence inspection can be omitted; thus the present invention can save time.

The above-described embodiments of the present invention are intended to be illustrative only. Numerous alternative embodiments may be devised by those skilled in the art without departing from the scope of the following claims.

What is claimed is:

1. A method for inspecting a grating biochip, comprising:
   irradiating a light beam having a predetermined wavelength to a grating biochip at a plurality of incident angles;
   measuring a diffracted light by using a photodetector at a plurality of receiving angles to generate a measurement signal with a function of an incident angle of the light beam and structural parameters of the grating biochip, wherein the receiving angles of the photodetector change as the incident angles change, and the diffracted light is generated by the light beam passing the grating biochip;
   selecting a plurality of parameters of the grating biochip; and
   optimizing the parameters to enhance detection sensitivity.

2. The method for inspecting a grating biochip as claimed in claim 1, wherein the light beam is generated by a focused laser source.

3. The method for inspecting a grating biochip as claimed in claim 1, wherein the light beam is generated by a linear laser source.

4. The method for inspecting a grating biochip as claimed in claim 1, wherein the light beam is generated by a planar laser source.

5. The method for inspecting a grating biochip as claimed in claim 1, wherein the grating biochip comprises a grating structure including:
   a semiconductor substrate;
   a grating positioned on the semiconductor substrate; and
   a dielectric layer covering the grating and the semiconductor substrate.

6. The method for inspecting a grating biochip as claimed in claim 5, wherein the dielectric constant of the dielectric layer is higher than that of the grating.

7. The method for inspecting a grating biochip as claimed in claim 5, wherein the grating biochip further comprises a single sample positioned on the grating structure.

8. The method for inspecting a grating biochip as claimed in claim 5, wherein the grating biochip comprises a plurality of grating structures and samples arranged in a one-dimensional array.

9. The method for inspecting a grating biochip as claimed in claim 5, wherein the grating biochip comprises a plurality of grating structures and samples arranged in a two-dimensional array.

10. The method for inspecting a grating biochip as claimed in claim 5, wherein the grating is made of silicon-oxygen compound.

11. The method for inspecting a grating biochip as claimed in claim 5, wherein the grating is made of silicon-nitrogen compound.

12. The method for inspecting a grating biochip as claimed in claim 5, wherein the dielectric layer is made of silicon-nitrogen compound.

13. The method for inspecting a grating biochip as claimed in claim 5, wherein the dielectric layer is made of poly-silicon material.

14. The method for inspecting a grating biochip as claimed in claim 1, wherein the step of optimizing the parameters comprises:
    determining a primary parameter and a plurality of subordinate parameters from the parameters;
    using a rigorous coupled wave algorithm to find a first subordinate parameter combination enabling the grating biochip to have the first optimal sensitivity as the primary parameter is a first default value;
    using the rigorous coupled wave algorithm to find a second subordinate parameter combination enabling the grating biochip to have a second optimal sensitivity as the primary parameter is a second default value; and
    comparing the first optimal sensitivity with the second optimal sensitivity to determine an optimal subordinate parameter combination.

15. The method for inspecting a grating biochip as claimed in claim 14, wherein the grating biochip includes a grating, and one of the parameters is the period of the grating.

16. The method for inspecting a grating biochip as claimed in claim 14, wherein the grating biochip includes a grating, and one of the parameters is the line/space ratio of the grating.

17. The method for inspecting a grating biochip as claimed in claim 14, wherein the grating biochip includes a grating, and one of the parameters is the thickness of the grating.

18. The method for inspecting a grating biochip as claimed in claim 14, wherein the grating biochip includes a dielectric layer, and one of the parameters is the thickness of the dielectric layer.

* * * * *